(12) United States Patent
Claereboudt et al.

(10) Patent No.: US 8,916,838 B2
(45) Date of Patent: Dec. 23, 2014

(54) DEVICE AND METHOD FOR PARTICLE BEAM DELIVERY

(75) Inventors: Yves Claereboudt, Corbais (BE); Michel Closset, Avin (BE)

(73) Assignee: Ion Beam Applications SA, Louvain-la-Neuve (BE)

( * ) Notice: Subject to any disclaimer, the term of this patent is extended or adjusted under 35 U.S.C. 154(b) by 0 days.

(21) Appl. No.: 13/152,741

(22) Filed: Jun. 3, 2011

(65) Prior Publication Data

US 2011/0297850 A1    Dec. 8, 2011

Related U.S. Application Data

(60) Provisional application No. 61/352,008, filed on Jun. 7, 2010.

(51) Int. Cl.
*G21G 5/00* (2006.01)
*A61N 5/10* (2006.01)

(52) U.S. Cl.
CPC . *A61N 5/10* (2013.01); *A61N 5/103* (2013.01)
USPC .......... 250/492.3; 250/492.1; 378/65

(58) Field of Classification Search
CPC ................................ A61N 5/10; A61N 5/103
USPC ................ 250/492.1, 492.3; 378/65
See application file for complete search history.

(56) References Cited

U.S. PATENT DOCUMENTS 7,425,717 B2 *   9/2008   Matsuda et al. ........... 250/492.3
7,560,717 B2 *   7/2009   Matsuda et al. ........... 250/505.1
2004/0227104 A1 *  11/2004  Matsuda et al. ........... 250/492.1

(Continued)

FOREIGN PATENT DOCUMENTS

EP    1 584 353 A1    10/2005

OTHER PUBLICATIONS

Zhu, X. et al., "Intensity modulated proton therapy treatment planning using single-field optimization: The impact of monitor unit constraints on plan quality" Med. Phys. 37 (3) Mar. 2010.*

(Continued)

*Primary Examiner* — Nicole Ippolito
*Assistant Examiner* — Wyatt Stoffa
(74) *Attorney, Agent, or Firm* — Christopher Casieri

(57) ABSTRACT

The present invention relates to a particle therapy system that comprises a spot scanning system to irradiate with a particle beam a plurality of spots in a layer of a target with prescribed spot doses for each spot of the layer. The therapy system is further adapted to perform multiple paintings of the layer and to deliver partial spot doses to selected spots of the layer during each painting time so that each spot of the layer will have received its prescribed dose after completion of the multiple paintings. The therapy system further comprises means for setting the partial spot doses and the number of times that a spot will be selected for irradiation in the course of the multiple paintings to such values that any spot of the layer will never have to be irradiated with a partial dose which would fall below a minimum dose deliverable by the system, and this whatever the number chosen for the number of layer paintings.

The invention also relates to a corresponding irradiation method.

8 Claims, 8 Drawing Sheets

(56) References Cited

U.S. PATENT DOCUMENTS

| | | | |
|---|---|---|---|
| 2008/0002811 A1* | 1/2008 | Allison | 378/65 |
| 2008/0023644 A1* | 1/2008 | Pedroni | 250/400 |
| 2009/0236545 A1 | 9/2009 | Timmer | |
| 2010/0183121 A1* | 7/2010 | Riker et al. | 378/65 |
| 2010/0327188 A1* | 12/2010 | Bert et al. | 250/492.3 |
| 2011/0081001 A1* | 4/2011 | Gertner et al. | 378/65 |
| 2011/0291028 A1* | 12/2011 | Brand | 250/492.1 |
| 2011/0297849 A1* | 12/2011 | Bert et al. | 250/492.1 |
| 2011/0306818 A1* | 12/2011 | Bert et al. | 600/1 |
| 2012/0119114 A1* | 5/2012 | Brauer | 250/492.3 |

OTHER PUBLICATIONS

Zenklusen, Silvan; Pedroni E.; Meer D.; "Preliminary Investigation For Developing Repainted Beam Scanning on the PSI Gantry 2"; Symposium, May 24, 2008, pp. 1-13; PTCOG 47; Paul Scherrer Institut (PSI); Switzerland.

Seco, Joao, Robertson, Daniel, Trofimov, Alexei, Paganetti, Harald; "Breathing Interplay Effects During Proton Beam Scanning: Simulation and Statistical Analysis"; Physics in Medicine and Biology; Jun. 23, 2009; pp. N283-N294; vol. 54; Massachusetts, United States of America.

* cited by examiner

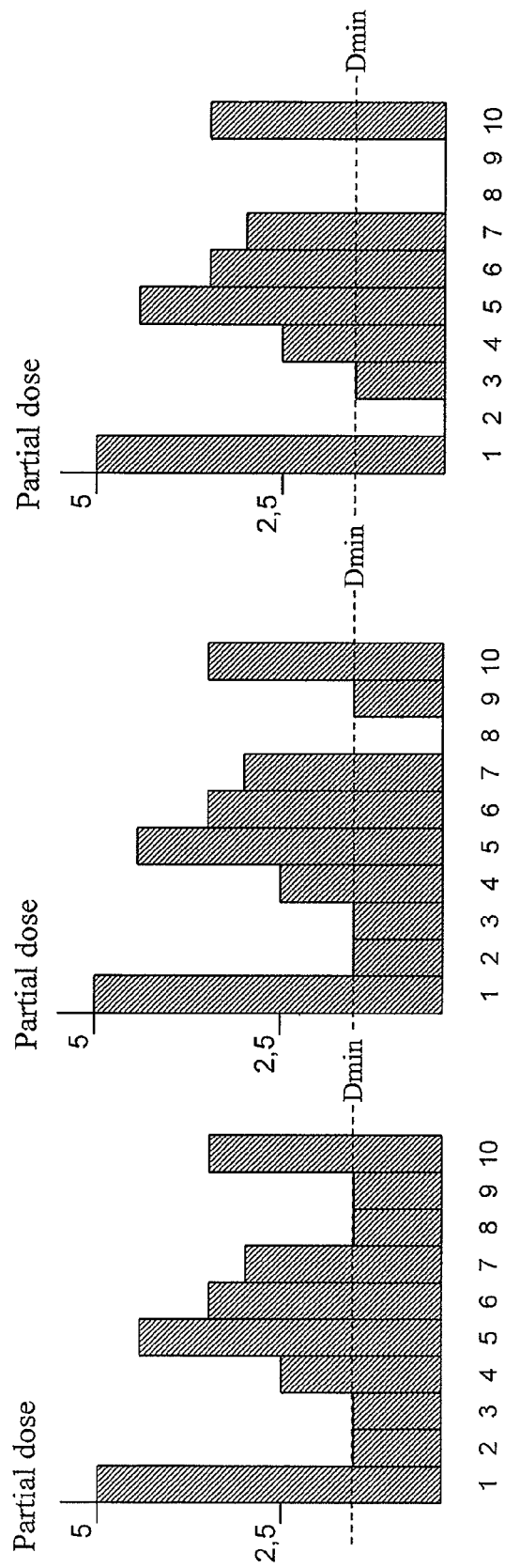

DEVICE AND METHOD FOR PARTICLE BEAM DELIVERY

CROSS-REFERENCE TO RELATED APPLICATION

This application claims the benefit of U.S. Provisional Patent Application No. 61/352,008, filed Jun. 7, 2010.

BACKGROUND OF THE INVENTION

1. Field of the Invention

The present invention relates to a particle therapy system designed for radiotherapy.

More particularly, the present invention concerns a particle therapy system for irradiating with a particle beam a plurality of spots in a layer of a target, said system comprising means for scanning the particle beam over said layer a prescribed number of layer scanning times (Nlayer_painting), and for irradiating selected spots of said layer with partial spot doses (Dspot_partial) in the course of each said layer scanning time so that each spot respectively receives a prescribed total spot dose (Dspot) after completion of the prescribed number of layer scanning times, said system being only able to irradiate a spot with a spot dose which is larger than or equal to a minimum spot dose (Dmin).

Dmin is the smallest dose which the therapy system can deliver to a spot of the target with an accuracy that is adequate for particle therapy. Such minimum spot dose (Dmin) is a feature of the particle therapy system which originates from its particular design. It may for example originate from its dosimetry equipment which has a specific operating range where the accuracy of dose measurement is guaranteed, or from its beam position detector which needs a minimum number of statistically relevant particle counts to determine the position of the beam with the required accuracy, or form limitations with respect to the delivery and control of the particle beam intensity.

The invention also concerns a method for irradiating a target with a particle beam.

2. Description of Prior Art

Such a particle therapy system is known for example from M. Phillips et al. in "Effects of respiratory motion on dose uniformity with a charged particle scanning method", Phys. Med. Biol., 1992, vol 37, No 1, 223-234 or from Pedroni et al. in "A novel gantry for proton therapy at the Paul Scherrer Institute", Cyclotrons and their applications 2001.

As discussed by Phillips et al., the use of scanned beams for irradiating a target can, due to organ motion, result in "cold" and "hot" dose areas. They showed that when a layer of the target volume is scanned (sometimes also called "painted") a plurality of times and when spots are irradiated with partial doses in the course of each scanning ("painting") time, the dose uniformity improves roughly with the square root of the number of scannings ("paintings").

Similarly, also Bortfeld, et al. in "Effects of intra-fraction motion in IMRT dose delivery: statistical analysis and simulation", Phys. Med. Biol. 47 (2002), pages 2203-2220, have studied the effect of organ motion on the dose uniformity when using a multiple painting spot scanning technique.

With the therapy systems disclosed by both Phillips et al. and Bortfeld et al., the partial spot dose of a spot (Dspot_partial) is obtained by dividing the prescribed total irradiation dose of said spot (Dspot) by the number of times the target is to be scanned/painted (Nlayer_painting). Hence, at each scanning time, a spot will be irradiated with the same partial dose.

However, Phillips et al. and Bortfeld et al. do not provide any information on what range of values should be selected for Nlayer_painting and they do not take into account the influence of a particular value of Nlayer_painting on the feasibility or accuracy of the delivery of the partial doses by a real particle therapy system. In particular, the particle therapy system will not be able to deliver partial spot doses which are smaller than the minimum spot dose (Dmin) or it will not be able to deliver them with sufficient accuracy.

This problem becomes even more relevant in case the distribution of the prescribed total spot doses is non-homogenous, i.e. when some spots of the target have a high and others a low prescribed total dose, which is often the case with spot scanning systems. The case being, when applying the teaching of Phillips et al. and Bortfeld et al., the number of layer paintings would logically be set to a relatively large value in order to reduce the effects of organ motion and, hence, this will increase the risk that the partial spot doses will fall below the minimum spot dose Dmin for those spots having a low prescribed total spot dose.

Patent document EP1477206 also discloses such a known particle therapy system, though no organ motion problems are addressed in this document. Instead, EP1477206 addresses a problem related to the inaccuracy of dose delivery that is caused by limitations of a capacitor used by a dose detector of the system. To solve this problem, this document discloses a particle therapy system wherein the number of layer paintings are set to a value which depends on a reference spot dose, which itself depends on the design of the apparatus, such as the design of the dose monitoring system. Such reference dose is a dose which this system can effectively deliver with a required accuracy.

With such a system, the partial spot doses are set to a value which is close to said reference dose, but the drawback is that the number of layer paintings cannot be freely chosen. Hence, one cannot optimize the number of layer paintings on the basis of other criteria such as for the reduction of effects for organ motion, or for reducing the treatment time.

There is thus room for improvement of the known particle therapy systems.

SUMMARY OF THE INVENTION

It is an object of the present invention to provide a particle therapy system and method wherein the number of layer paintings (Nlayer_painting) can be more freely chosen, yet making sure that, for any value which will be selected for Nlayer_painting, the partial spot doses (Dspot_partial) will all be higher or equal to the minimum spot dose (Dmin).

To this end, the particle therapy system according to the invention is characterized in that it further comprises means for determining, for each spot of said layer, the partial spot doses (Dspot_partial) and a number of times that said spot is to be selected for irradiation (Nspot_painting), according to both the following rules a) and b):

a) each of the partial spot doses (Dspot_partial) is larger or equal to Dmin,
b) if (Dspot/Nlayer_painting>=Dmin), then (Nspot_painting=Nlayer_painting), else (Nspot_painting<Nlayer_painting).

Thus, with a particle therapy system according to the invention, the number of layer paintings (Nlayer_painting) can indeed be freely chosen and, whatever the value chosen, the number of times a spot will be selected for irradiation (Nspot_painting) will be adapted in such a way that its partial spot doses will always be larger or equal to the minimum dose (Dmin).

In particular, if it turns out that irradiating a spot Nlayer_painting times with partial spot dose equal to Dspot/Nlayer_painting would lead to partial spot doses (Dspot_partial) which are inferior to the minimum dose (Dmin), (i.e. if the condition of rule b) is satisfied) then the system according to the invention will determine that said spot is to be selected for irradiation less than Nlayer_painting times with partial spot doses which are always all larger than or equal to the minimum dose (Dmin).

Accordingly, whatever the value chosen for Nlayer_painting, the system will always be able to effectively deliver the partial spot doses, yet making sure that each spot will receive its prescribed total spot dose after completion of the chosen number of layer scanning times.

A system according to the invention has the additional advantage that, for those spots for which Dspot/Nlayer_painting>=Dmin (i.e. when a prescribed total dose of a spot is high compared to the minimum dose deliverable by the system), the number of times these spots will be selected for irradiation (Nspot_painting) is exclusively determined by a freely chosen number of layer paintings (Nlayer_painting).

In contrast, in prior art document EP1477206, this the number of spot paintings (Nspot_painting) depends on a reference dose value which is not freely chosen, so that, in case the prescribed total spot dose (Dspot) is high compared to said reference dose value, the number of spot paintings will become high too, resulting in long treatment times.

With a system according to the invention, the number of spot paintings—and hence the overall irradiation time or treatment time—may therefore be reduced compared to a system according to EP1477206.

It is a further object of the invention to maximise the number of spot paintings (Nspot_painting) for a given number of layer paintings (Nlayer_painting), while at the same time taking into account the constraint of the minimum deliverable spot dose (Dmin). Maximizing the number of spot paintings reduces indeed the effects of organ motion as explained previously.

To this end, the particle therapy system according to the invention is preferably characterised in that Nspot_painting is determined according to the following rule:

if (Dspot/Nlayer_painting>=Dmin), then (Nspot_painting=Nlayer_painting), else (Nspot_painting=Floor(Dspot/Dmin)).

The function "Floor" is a function that delivers the largest integer not larger than its argument. Hence, with such a preferred system, the partial spot doses will always be larger than or equal to Dmin, and the number of spot paintings will be either equal to the number of layer paintings or to the largest possible integer not larger than the number of layer paintings.

The invention also concerns a method for irradiating a target with a particle beam as specified in the claims.

BRIEF DESCRIPTION OF THE DRAWINGS

These and further aspects of the invention will be explained in greater detail by way of example and with reference to the accompanying drawings in which:

FIG. 8A, FIG. 8B, FIG. 8C show an example of a division of an irradiation into respectively three paintings following the spot dose division of FIG. 7.

The figures are not drawn to scale. Generally, identical components are denoted by the same reference numerals in the figures.

DETAILED DESCRIPTION OF PREFERRED EMBODIMENTS

Figure 1:
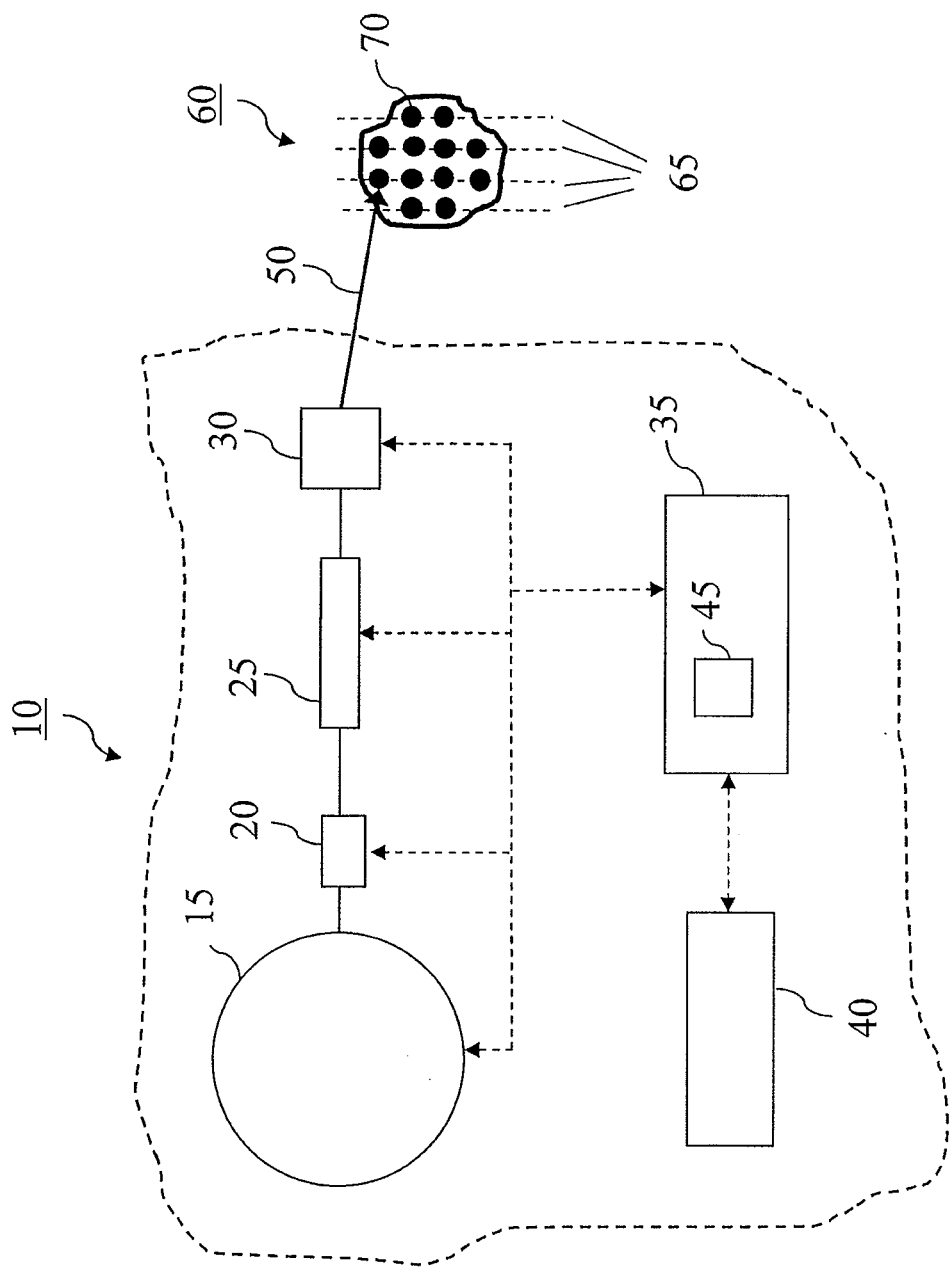
FIG. 1 shows a schematic representation of a particle therapy system according to the invention.

FIG. 1 shows a schematic representation of an exemplary particle therapy system (10) comprising an accelerator (15) for producing an energetic charged particle beam, an energy selection system (20) to vary the energy of the beam, a beam transport system (25) to transport the beam to a treatment room and a scanning nozzle (30) for scanning the beam (50) over a target (60). The particle therapy system further comprises a control system (35) for controlling the various components of the apparatus such as the accelerator, the energy selection system, the beam transport system, the scanning nozzle, and possibly other components or subcomponents of the apparatus.

The therapy system furthermore comprises a treatment planning system (40) which interfaces with the control system (35). The treatment planning system creates a treatment plan comprising treatment planning information, i.e. input parameters for performing a target irradiation.

For the further discussion and examples given, it is assumed that the treatment planning system has virtually divided the target (60) in layers (65) and that, for each layer, it has defined spots (70) (e.g. identified with position coordinates) and has prescribed associated total spot doses (Dspot). Generally, a layer of a target is specified by the energy of the particle beam, i.e. all spots of a same layer are irradiated with a particle beam (50) having the same energy. Varying the selection of a layer corresponds to varying the energy of the particle beam using e.g. the energy selection system (20).

The system is adapted to perform multiple layer paintings, i.e. to scan the particle beam over a layer (65) of the target a prescribed number of layer scanning times (Nlayer_painting) so that the total spot dose (Dspot) is not delivered within a single irradiation but instead the spots receive partial spot doses (Dspot_partial) in the course of the multiple layer paintings.

A parameter of the system is the layer painting number (also named the number of layer scanning times) (Nlayer_painting), which specifies the number of layer paintings or the number of layer scanning times to be performed for each layer. A layer painting or layer scanning time is hereby defined as an irradiation of a series of selected spots of a layer for delivering partial spot doses (Dspot_partial) to the spots of the series. In this example, the layer painting number can be an additional parameter of the treatment plan where a layer painting number is prescribed for each layer, or it can be a single number prescribing an overall painting number for painting the target volume a number of times. In the latter case, the same value of the number of paintings prescribed can for example be adopted for specifying a layer painting number for each layer of the target volume.

Figure 2:
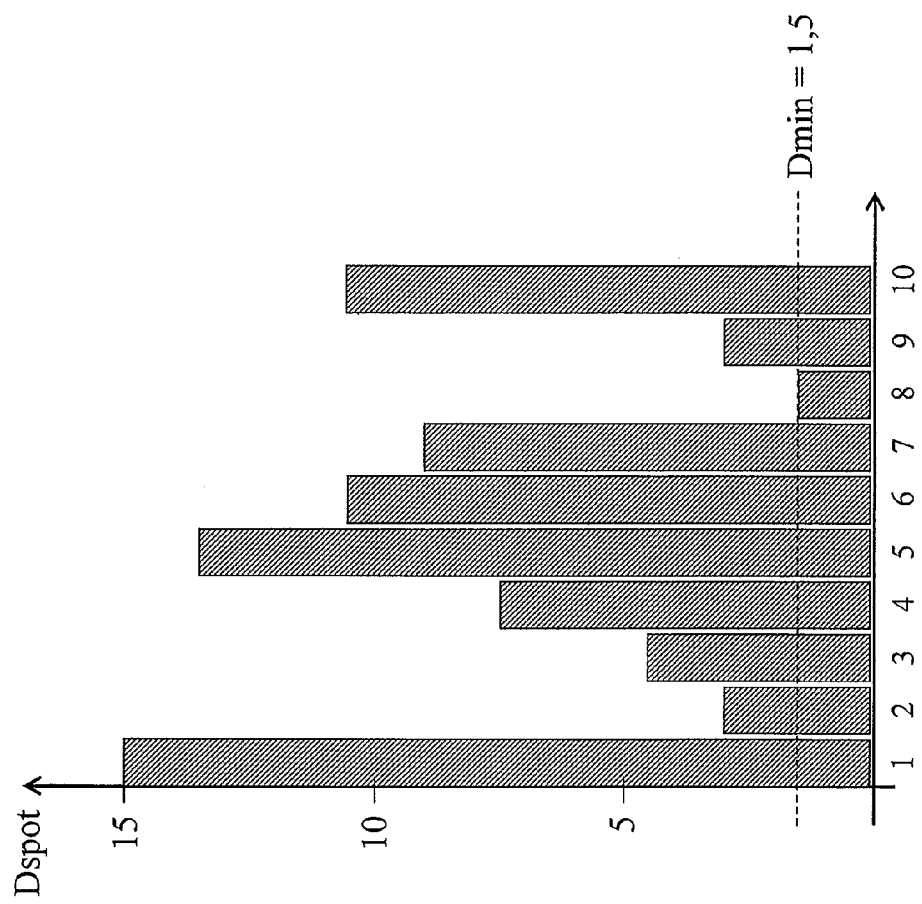
FIG. 2 shows an example of prescribed total spot doses for a series of ten spots.

The prescribed total spot dose (Dspot) for each spot as prescribed by the treatment planning system (40) can vary from spot to spot. This is illustrated in FIG. 2 where for example ten spots (i=1 to 10) are schematically represented with their corresponding prescribed spot dose (Dspot(i)) of respectively 15; 3; 4.5; 7.5; 13.5; 10.5; 9; 1.5; 3 and 10.5 (arbitrary units are used). These dose values can for instance represent an absolute dose or a relative dose representing a weight or a percentage. These ten spots in FIG. 2 represent for example a series of spots having positioning coordinates x, y and belonging to a layer of the target volume (60). In practice, the number of spots defined for a layer in a treatment plan is much higher (e.g. can be thousands of spot positions) and depends for example on the size of the target to be irradiated and the size of the scanning particle beam.

Figure 3A:
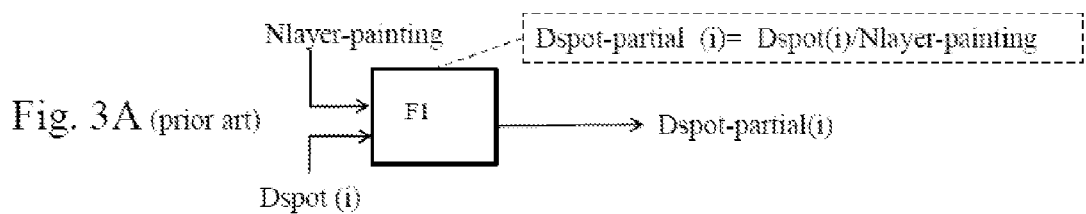
FIG. 3A shows schematically one painting strategy according to the prior art.
Figures 4A, 4B, 4C:
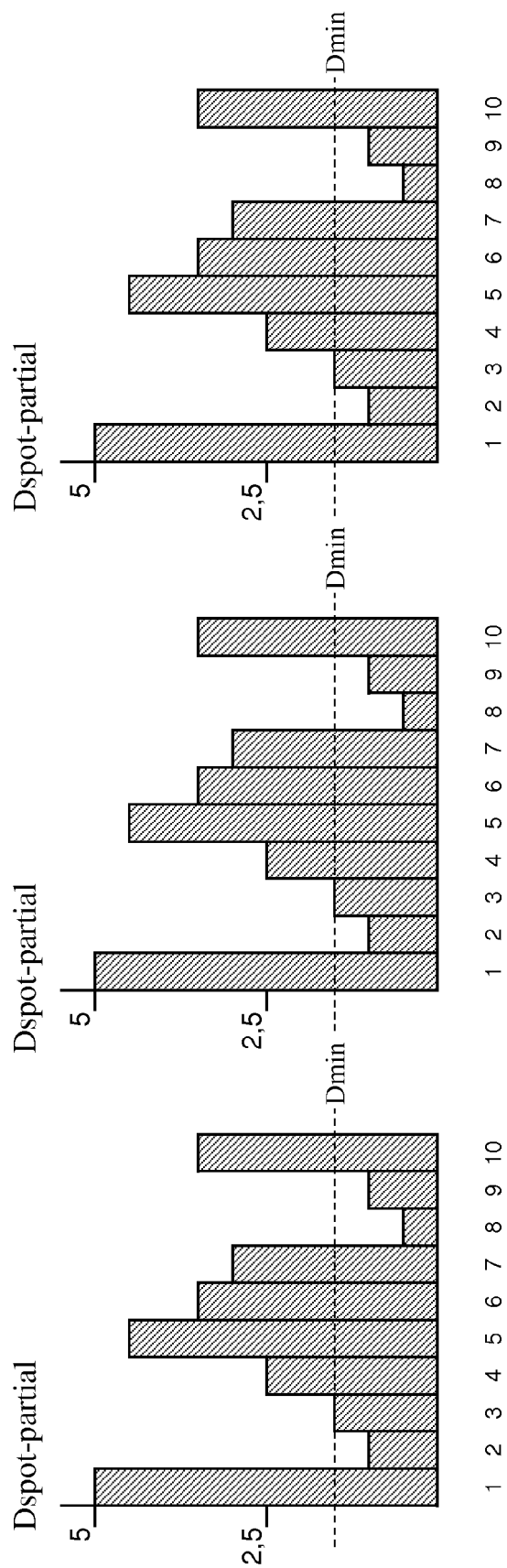
FIG. 4A, FIG. 4B and FIG. 4C show an example of a division of an irradiation into respectively three paintings following a prior art painting strategy.

FIG. 3A summarizes the painting strategy according to Phillips et al. and Bortfeld et al. For each spot i, the partial spot dose Dspot_partial(i) is based on input parameters Nlayer_painting and total spot dose Dspot(i). As an example, suppose that the layer painting number Nlayer_painting prescribed for a layer is three, then the prescribed spot dose is divided by three in order to deliver the prescribed total dose Dspot(i) to the spots i following completion of three subsequent paintings. In this case, each spot i receives a partial dose Dspot_partial(i) equal to one third of the prescribed dose Dspot(i) during each layer painting. As an example, the painting strategy of FIG. 3A has been applied to the ten spots of FIG. 2 while adopting for Nlayer_painting a value of three. This is illustrated in FIG. 4A, FIG. 4B and FIG. 4C where the resulting partial spot doses Dspot_partial are plotted for layer painting #1, layer painting #2 and layer painting #3, respectively.

Figure 5:
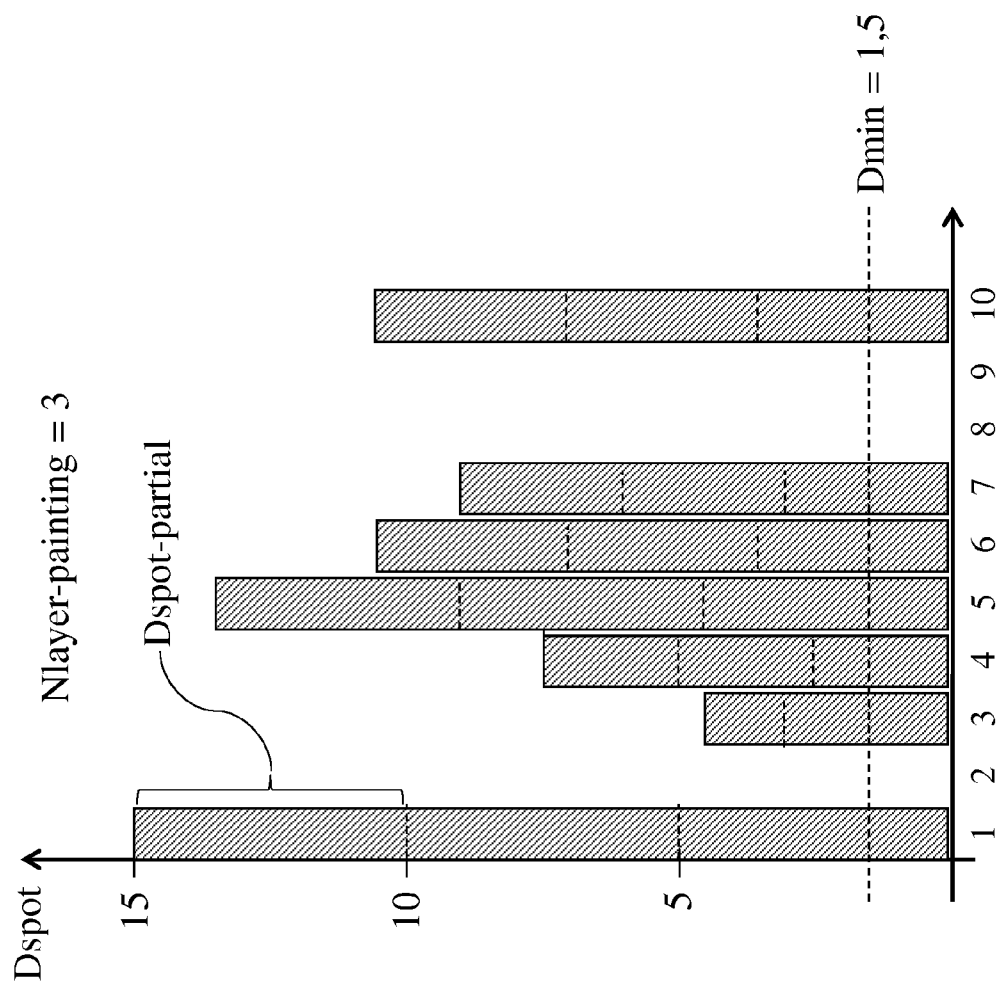
FIG. 5 shows the resulting spot dose that can be delivered by a particle therapy system to the ten spots of FIG. 2 when applying the prior art painting strategy of FIG. 3A.

As discussed above, the particle therapy system (10) has a constraint that no spot irradiation can be performed if the spot dose to be delivered is below a minimum value Dmin. In the example discussed above, the value of Dmin was for example taken to be 1.5 (expressed in arbitrary units) and is illustrated with a horizontal dotted line in FIG. 4A, FIG. 4B and FIG. 4C. In this example, the partial spot doses (Dspot_partial(i)) of spot positions 2, 8 and 9 are smaller than Dmin. As a consequence, a particle therapy system being limited by a Dmin value of 1.5 cannot deliver the partial spot doses of spots 2, 8 and 9. This is illustrated in FIG. 5 showing the resulting delivered spot doses that would be delivered with the particle therapy system when following the painting strategy of FIG. 3A. As no spot dose can be delivered to spots 2, 8, 9, large errors in the dose distribution will occur. In practice, such an irradiation should not be performed and the treatment plan should be refused.

According to the present invention, a controller or computer (45) is for example added to the particle therapy system to divide the layer irradiations into the number of layer scanning times prescribed while at the same time taking into account the constraint Dmin of the particle therapy system.

For each spot of a given layer, the controller (45) will calculate a number of times the spot is to be selected for irradiation with a partial spot dose in the course of a layer scanning. This number of times a spot is selected for irradiation is named the number of spot paintings (Nspot_painting). The controller will also determine, for each time a spot is selected for irradiation, a corresponding prescribed partial spot dose (Dspot_partial).

Figure 6A:
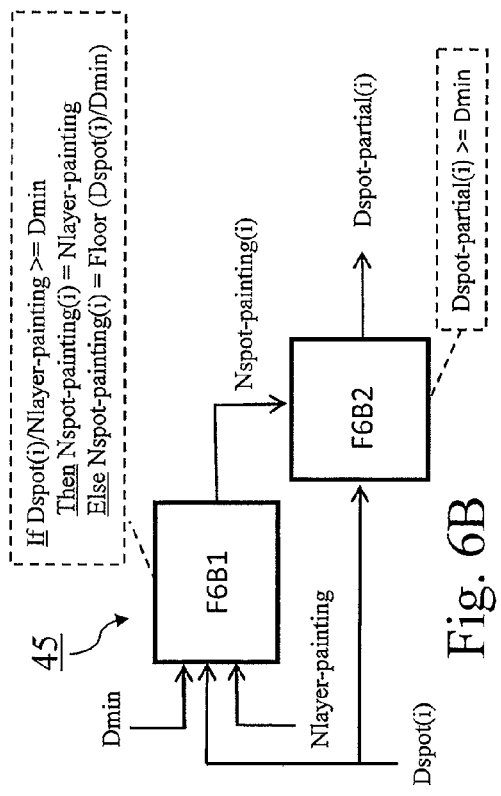
FIG. 6A, FIG. 6B and FIG. 6C illustrate schematically a controller using algorithms according to the invention.

The calculations performed by controller (45) are schematically illustrated in FIG. 6A. An algorithm F6A is used, in a first stage, for calculating, for a given layer, the number of spot paintings Nspot_painting(i). For each spot i of a given layer, having a prescribed total spot dose Dspot(i) the following steps are executed by algorithm F6A:

Step 1 Calculate Dratio(i) = Dspot(i)/Nlayer_painting
Step 2 Compare Dmin with Dratio(i)
    If Dratio(i) >=Dmin, then
        Nspot_painting(i) = NLayer_painting,
        else
        Nspot_painting(i) < Nlayer_painting.

Furthermore, when Dratio(i)<Dmin, the number of spot paintings cannot be selected to be any arbitrary value lower than Nlayer_painting. For example, if Nlayer_painting=5 and Dmin=3, then, for a spot i having a prescribed spot dose Dspot=10 and, using the above algorithm, it is determined that Dratio(i)=2 and the number of spot paintings should be lower than Nlayer_painting=5. In this example, Nspot_painting(i) can however not be selected to be 4 because Dspot=10 cannot be divided into four partial spot doses such that each partial spot dose is larger than Dmin=3.

The constraint that all partial spot doses shall be equal or larger than Dmin has as a consequence that, for the cases where Dratio(i)<Dmin, the number of spot paintings is limited by a maximum value MaxNspot_paintings(i) that is depending on Dmin:

$$N\text{spot\_painting}(i) <= \text{Max}N\text{spot\_painting}(i)$$

where MaxNspot_painting(i) is the largest integer lower than Nlayer_painting such that Dspot(i)/MaxNspot_painting(i)>=Dmin. Mathematically, this corresponds to:

$$\text{Max}N\text{spot\_painting}(i) = \text{Floor}(D\text{spot}(i)/D\text{min}),$$

where the function "Floor" is a function delivering the largest integer not larger than its argument. For example, Floor(3,33)=3.

The number of spot paintings for the case that Dratio(i)<Dmin, can then be selected between 1 and MaxNspot_painting(i).

In the example given above, for spot i having a spot dose of Dspot(i) of 10 and Dmin=3, MaxNspot_painting(i)=Floor (10/3)=3 and hence Nspot_painting(i) will be an integer number selected among 1, 2 and 3.

The selection of a particular value for the number of spot paintings among the various calculated values may be performed by the controller (45) or by another part of the therapy system (10) on the basis of any kind of appropriate criteria, such as for example the treatment time, the effects of organ motion, or other criteria which one would wish to impose on the partial spot doses on top of those indicated hereunder.

After selecting or receiving a particular number of spot paintings, the partial spot doses to be delivered for each spot i during each of these spot paintings (Dspot-partial(i)) are determined by the controller (45) during a second stage of the calculation as follows:

For each spot i of a given layer, having a prescribed total spot dose Dspot(i), the calculation performed by controller (45) will take the following constraints into account:
  The sum of all partial spot doses Dspot_partial(i) shall be equal to the prescribed total spot dose Dspot(i).
  The partial spot doses Dspot_partial(i) shall all be equal or larger than the minimum spot dose Dmin.

Figure 6B:
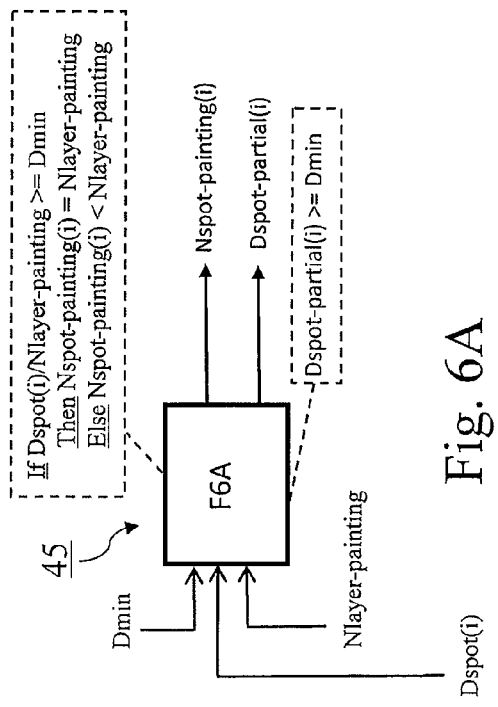

An example of a controller (45) according to a preferred embodiment of the invention is shown in FIG. 6B. In this preferred embodiment, Step 2 of algorithm F6A is performed as follows:

```
If Dratio(i) >=Dmin, then
    Nspot_painting(i) = NLayer_painting,
        Else
    Nspot_painting(i) = Floor(Dspot(i)/Dmin).
```

The function "Floor" is, as discussed above, a function delivering the largest integer not larger than its argument. So for example Floor(1.3)=1 and Floor(2,9)=2. With such an algorithm, Nspot_painting(i) will always be lower than Nlayer_painting for those spots i for which Dratio(i)<Dmin.

Figure 6C:
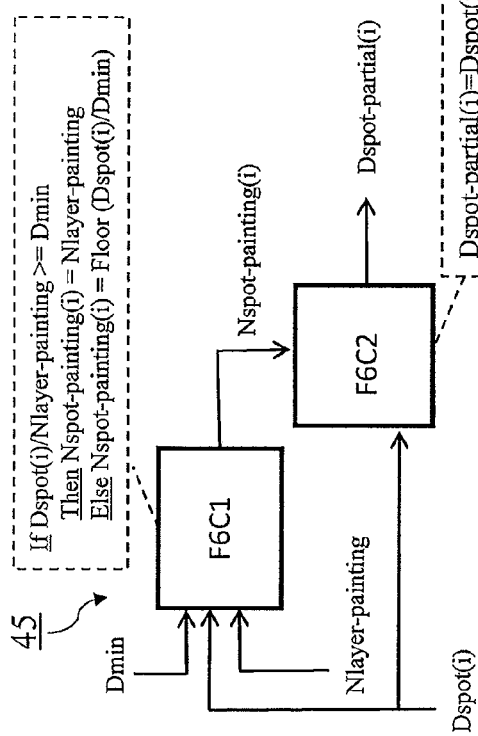

An example of a controller (45) according to a more preferred embodiment of the invention is shown in FIG. 6C. In this preferred embodiment, after having determined the number of spot paintings (Nspot_painting(i)) according to the algorithm of FIG. 6B, the partial spot doses to be delivered to each spot i during each of these spot paintings is calculated as follows:

$$Dspot\_partial(i)=Dspot(i)/Nspot\_painting(i).$$

With this more preferred embodiment, each spot will receive a same amount of partial dose a plurality of times.

Figure 7:
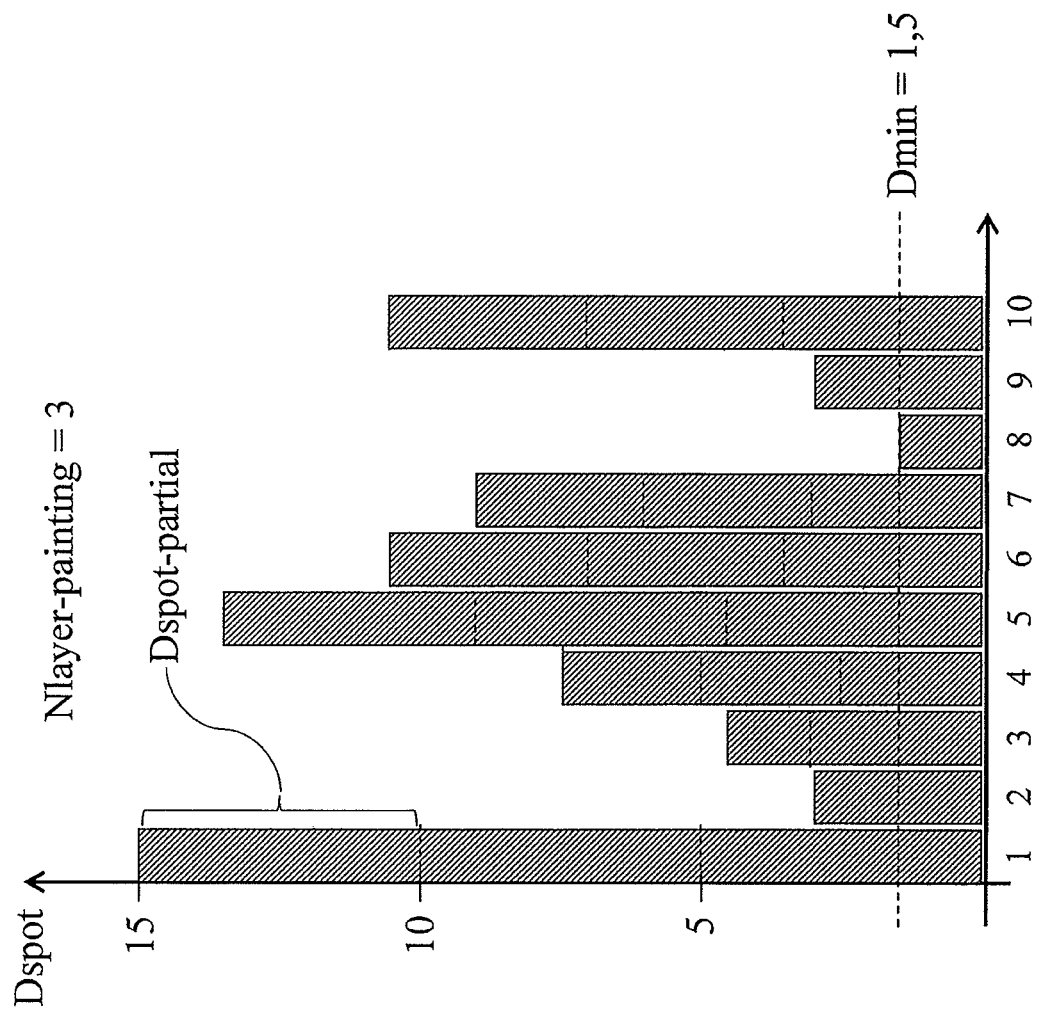
FIG. 7 illustrates an exemplary division of prescribed total spot doses of a series of ten spots into partial spot doses according to the invention.

FIG. 7 illustrates an example of the results of a division of the irradiation into paintings by the preferred controller shown in FIG. 6C. For this example, the same ten spots (i=1 to 10) and corresponding total spot doses Dspot(i) of FIG. 2 were used as an input. Again, three layer paintings (i.e. Nlayer_painting=3) are assumed to be prescribed (specified on treatment planning level for instance).

The controller (45) first calculates, for each spot i, the number of spot paintings Nspot_painting(i) following the algorithm F6C1 discussed above and illustrated in FIG. 6C. For the spots i=2, 8 and 9, the value of Dratio(i) is smaller than the value of Dmin and hence the controller will calculate that these spots will be irradiated Floor(Dspot(i)/Dmin) times, which in this example results in respectively 2, 1 and 2 times. In other words, this means that spots 2, 8 and 9 are selected respectively two times, one time and two times for irradiation with a partial spot dose. For the other spots, Dratio(i) is larger than Dmin, so that these other spots are selected NLayer_painting times for irradiation, namely three times in this example.

The controller (45) then calculates for each spot i the partial spot doses Dspot_partial(i) following the algorithm F6C2 discussed above and illustrated in FIG. 6C. The division of the total spot doses Dspot(i) into partial spot doses Dspot_partial(i) is illustrated for each spot by a dotted/dashed horizontal line. For example, the total dose of spot 1 is divided into three parts (Nspot_painting(1)=3), the total dose of spot 2 is divided into two parts (Nspot_painting(2)=2), and the total dose of spot 8 is kept as one single dose (Nspot_painting(8)=1). This means that spot position 2 will be two times part of a layer painting and spot position 8 will only be once part of a layer painting.

It will be appreciated that, in a system according to the invention, the number of spot paintings (Nspot_painting) (also named "number of spot irradiations", or "number of times a spot is selected for irradiation") might, for one or more spots, be lower than the number of layer paintings (Nlayer_painting).

The determination of which spots of a layer are painted or irradiated during which painting time of said layer is described hereafter for a most preferred embodiment of a therapy system (10) according to the invention, This most preferred embodiment comprises means for determining which spots of the layer are to be selected for irradiation with their respective partial spot doses in the course of each painting or scanning time. These means for grouping spot paintings into layer paintings will be further described using the example of FIG. 7 and the results of a preferred grouping are illustrated in FIG. 8 A, FIG. 8 B and FIG. 8 C for layer painting 1, layer painting 2 and layer painting 3, respectively. To obtain the grouping illustrated in FIGS. 8A, 8B and 8C, it is determined what spot of the layer is belonging to what layer painting or what scanning time of the layer. For the first layer painting, the maximum number of spots that need to receive a partial spot dose are first selected and grouped together for forming a first layer painting. In other words, this means that if Dspot(i) is larger than Dmin for all spots of the layer, the first layer painting will always comprise a partial irradiation of all spots of the layer. This is illustrated in FIG. 8 A where, for each spot of the layer irradiation, the partial dose that will be delivered during the course of the first layer painting is plotted. In this example, during the first layer painting, all spots from 1 to 10 are indeed part of this first layer painting because all of the points were selected to be irradiated at least one time. For the second painting one again looks what the remaining maximum number of spots are that need a further partial dose to be delivered and those are grouped together in a subsequent layer painting. In the example of FIG. 7, these are spots 1, 2, 3, 4, 5, 6, 7, 9, 10 because these spots were selected to be irradiated two times or more. FIG. 8 B illustrates, for each spot of the layer irradiation, the partial dose that will be delivered during the course of the second layer painting. Spot 8 is not part of the layer painting 2 as no partial dose needs to be delivered to spot 8 anymore during layer painting 2 (Nspot_painting(8)=1). Preferably, the beam scanning process will omit this spot position 8 and the spot scanning process will for example go from position 7 to position 9 without the need for going to position 8 as there is no partial dose to be delivered for position 8 during painting 2. For the third layer painting, which in this example is the last layer painting, the remaining spots having an Nspot_painting(i) value equal to 3 are grouped as a sequence of spots for forming the last layer painting. In the example of FIG. 7, these are spots 1, 3, 4, 5, 6, 7 and 10 because these spots were selected to be irradiated three times. FIG. 8 C illustrates, for each spot of the layer irradiation, the partial dose that will be delivered during the course of the third layer painting. In the example given, there are in total 10, 9 and 7 spot irradiations during the course of layer paintings 1, 2 and 3, respectively.

In summary, the following algorithm is preferably used to mathematically determine what spot is belonging to what layer painting or layer scanning time and hence group spots into series of spots that belong to layer paintings or layer scanning times:

```
Layer Scanning time #1:
    all spots i having Nspot_painting(i) = 1 to Nlayer_painting
Layer Scanning time #2:
    all spots i having Nspot_painting(i) = 2 to Nlayer_painting
...
Layer Scanning time #Nlayer_painting – 1:
    all spots i having Nspot_painting(i) =
        NLayer_painting – 1 to NLayer_painting
Layer Scanning time #Nlayer_painting:
    all spots i having Nspot_painting = Nlayer_painting
```

When the layer paintings or layer scanning times are defined, the sequence of layer paintings or scanning times to be executed by the particle therapy system can still be selected. For example, instead of sequentially executing layer painting 1, 2 and 3 as shown in FIG. 8, one can as well make permutations and sequentially execute layer paintings 1, 3, 2 or 2, 3, 1 or 2, 1, 3 or 3, 2, 1 or 3, 1, 2. Moreover, one can also perform so called 3D paintings where one first makes sequentially the first layer painting for each layer of the target volume and then starts again at the first layer with the second layer painting, then the second layer painting of the second layer and one continues like this until all layer paintings of all layers are completed.

The controller (45) of the particle therapy system can for example be part of the control system (35) or it can be part of the treatment planning system (40).

In the latter case the treatment planning system (40) may comprise information on the constraint Dmin of the particle therapy system (10) and the treatment planning system calculates the prescribed partial spot doses for each spot of each layer painting. In the former case, the control system (35) may receive a treatment plan from the treatment planning system (40) comprising the total spot doses Dspot(i) for all spots of a layer without division in partial doses. In this case, the control system calculates the partial spot doses Dspot_partial(i) using inputs from the treatment planning system (40), i.e. for each layer, the number of layer paintings or number of layer scanning times (Nlayer_painting) and, for each spot i of each layer, the total spot doses Dspot(i). The value Dmin, needed for determining the partial spot doses, may in this case be a value that for example is stored in a memory of the control system (35) or it can be a value that is hard-coded in software implementing the algorithms described above.

The interface between the treatment planning system (40) and the control system (35) can for example be based on a standard protocol used for communication of data between systems used in medical radiotherapy. A currently available standard protocol for radiation therapy is DICOM-RT and more particular for particle therapy it is DICOM-RT ion. When using a Dicom-RT ion protocol an RT Ion Plan is created by the treatment planning system defining a large number of parameters for performing an irradiation. One of these parameters of the treatment plan is specifying a number of layer paintings for each layer which, in Dicom-RT ion, is specified through code (300A, 039A).

The present invention has been described in terms of specific embodiments, which are illustrative of the invention and not to be construed as limiting. More generally, it will be appreciated by persons skilled in the art that the present invention is not limited by what has been particularly shown and/or described herein. The invention resides in each and every novel characteristic feature and each and every combination of characteristic features.

Reference numerals in the claims do not limit their protective scope. Use of the verbs "to comprise", "to include", "to be composed of", or any other variant, as well as their respective conjugations, does not exclude the presence of elements other than those stated. Use of the article "a", "an" or "the" preceding an element does not exclude the presence of a plurality of such elements.

Summarized, the invention may also be described as follows: A particle therapy system (10) that comprises a spot scanning system to irradiate with a particle beam (50) a plurality of spots (70) in a layer (65) of a target (60) with prescribed spot doses for each spot of the layer. The therapy system is further adapted to perform multiple paintings of the layer (65) and to deliver partial spot doses to selected spots of the layer during each painting time so that each spot of the layer will have received its prescribed dose after completion of the multiple paintings. The therapy system further comprises means (45) for setting the partial spot doses and the number of times that a spot will be selected for irradiation in the course of the multiple paintings to such values that any spot of the layer will never have to be irradiated with a partial dose which would fall below a minimum dose deliverable by the system (10), and this whatever the number chosen for the number of layer paintings.

The invention also relates to a corresponding irradiation method.

The invention claimed is:

1. A method for irradiating with a particle beam (50) a plurality of spots in a layer (65) of a target (60), said method comprising the steps of:
   providing a particle therapy system (10) for irradiating the plurality of spots with the particle beam, said system being only able to irradiate a spot with a spot dose which is larger than or equal to a minimum spot dose (Dmin),
   scanning the particle beam over the layer a prescribed number of layer scanning times (Nlayer_painting),
   irradiating selected spots of said layer in the course of each said layer scanning time with partial spot doses (Dspot_partial), characterized in that, for each spot of the layer (65), the partial spot doses (Dspot_partial) and a number of times that said spot is to be selected for irradiation (Nspot_painting), are set by a), b) and c):
   a) making each of the partial spot doses (Dspot_partial) larger or equal to Dmin,
   b) making the sum of all partial spot doses (Dspot_partial) equal to a prescribed total spot dose (Dspot), and
   c) making Nspot_painting=Nlayer_painting if Nspot/Nlayer_painting>=Dmin, else making Nspot_painting<Nlayer painting.

2. A method according to claim 1, characterized in that Nspot_painting is set by c):
   c) making Nspot_painting=Nlayer_painting if Dspot/Nlayer_painting>=Dmin, else making Nspot_painting=Floor (Dspot/Dmin).

3. A method according to any of claim 1 or 2, characterized in that, for each spot of said layer, each of the partial spot doses (Dspot_partial) is set by rule a):
   a) making Dspot_partial=Dspot/Nspot_painting.

4. A method according to any of claim 1 or 2, characterized in that, for each scanning time of the layer, the following spots of said layer are selected for irradiation with their respective partial spot doses:

---

Layer scanning time #1:
    all spots having Nspot_painting = 1 to Nlayer_painting,
Layer scanning time #2:
    all spots having Nspot_painting = 2 to Nlayer_painting,
Layer scanning time # (Nlayer_painting−1):
    all spots having Nspot_painting = NLayer_painting − 1 to NLayer_painting, and
Layer scanning time #Nlayer_painting:
    all spots having Nspot_painting= Nlayer_painting.

---

5. A particle therapy system (10) adapted to irradiate with a particle beam (50) a plurality of spots (70) in a layer (65) of a target (60), said system (10) comprising:
   means (30) for scanning the particle beam over said layer a prescribed number of layer scanning times (Nlayer_painting),
   means for irradiating selected spots of said layer with partial spot doses (Dspot_partial) in the course of each said layer scanning time,
   said system (10) being only able to irradiate a spot with a spot dose which is larger than or equal to a minimum spot dose (Dmin),
   a controller (45) configured to receive as an input said prescribed number of layer scanning times (Nlayer_ painting), and, for each spot (70) of the layer, a corresponding prescribed total spot dose (Dspot), and wherein the controller (45) is configured to determine, for each spot (70) of said layer, the partial spot doses (Dspot_partial) and a number of times that said spot is to be selected for irradiation (Nspot_painting), and wherein the controller (45) is further configured to follow rules a), b) and c):

a) each of the partial spot doses (Dspot_partial) is larger or equal to Dmin,
b) the sum of all partial spot doses (Dspot_partial) shall be equal to the prescribed total spot dose (Dspot), and
c) if Dspot/Nlayer_painting>=Dmin, then Nspot_painting=Nlayer_painting, else Nspot_painting< Nlayer_painting.

6. A particle therapy system according to claim 5, wherein the controller is configured to follow rule c):

c) if Dspot/Nlayer_painting>=Dmin, then Nspot_painting=Nlayer_painting, else Nspot_painting=Floor (Dspot/Dmin).

7. A particle therapy system according to any of claim 5 or 6, wherein, the controller is configured to follow rule a):

a) Dspot_partial=Dspot/Nspot_painting.

8. A particle therapy system according to any of claim 5 or 6, further comprising means for determining which spots of the layer are to be selected for irradiation with their respective partial spot doses in the course of each scanning time of said layer configure to follow the sequence:

Layer scanning time #1:
    all spots having Nspot_painting = 1 to Nlayer_painting,
Layer scanning time #2:
    all spots having Nspot_painting = 2 to Nlayer_painting,
Layer scanning time # (Nlayer_painting−1):
    all spots having Nspot_painting = NLayer_painting − 1 to NLayer_painting, and
Layer scanning time #Nlayer_painting:
    all spots having Nspot_painting= Nlayer_painting.

\* \* \* \* \*